(12) United States Patent
Miyazaki

(10) Patent No.: US 8,014,989 B2
(45) Date of Patent: Sep. 6, 2011

(54) BIREFRINGENCE CALCULATING METHOD AND BIREFRINGENCE CALCULATING APPARATUS

(75) Inventor: Yosuke Miyazaki, Ichihara (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 543 days.

(21) Appl. No.: 11/437,650

(22) Filed: May 22, 2006

(65) Prior Publication Data

US 2007/0002320 A1    Jan. 4, 2007

(30) Foreign Application Priority Data

May 23, 2005 (JP) ................. P2005-149826
Mar. 28, 2006 (JP) ................. P2006-087991

(51) Int. Cl.
G06G 7/58 (2006.01)
G06F 13/10 (2006.01)
(52) U.S. Cl. .......................... 703/12; 703/21
(58) Field of Classification Search .............. None
See application file for complete search history.

(56) References Cited

FOREIGN PATENT DOCUMENTS

| JP | 11-281642 A | 10/1999 |
| JP | 2004-287812 | 10/2004 |
| JP | 2006-039164 | 2/2006 |
| JP | 2006-523351 T | 10/2006 |

OTHER PUBLICATIONS

Loriot et al., Atomic Level Picture of Stress Relaxation in Polymer Melts, Journal of Polymer Science: Part B: Polymer Physics, 1998, 36, 143-154.*
Gao et al., Monomer-Level Description of Stress and Birefringence Relaxation in Polymer Melts, Macromolecules, 1994, 27, 1201-1209.*
Jiang et al. (Optical Materials, 2006, 28, 189-194).*
Auhl et al. (Journal of Chemical Physics, 2003, 119(24), 12718-12728).*
Y. Aikawa, "Calculation Method of Estimate the Birefringence of Polymers and Their Experimental Validation", Japanese Journal of Polymer Science and Technology (Kobunshi Ronbunshu), vol. 51, No. 4, (1994), pp. 237-243 with Abstract.
M. Fukuda et al., "Molecular-dynamics simulation of moisture diffusion in polyethylene beyond 10 ns duration", J. Chem. Phys. 107, (1997), 2149-2159.
S. Kakou '05, "Molecular dynamics simulation on stretching of polymer films".
K. Morigami et al., Japanese Journal of Polymer Science and Technology (Kobunshi Ronbunshu), vol. 53, No. 12, (Dec. 1996), pp. 852-859.
K.G. Denbigh, Trans, Faraday Soc., 36, (1940), pp. 936-948.
D.W. Van Krevelan, Properties of Polymers, $2^{nd}$ Edition Elsevier, Amsterdam, (1976), pp. 56-59.

(Continued)

Primary Examiner — Marjorie Moran
Assistant Examiner — Larry D Riggs, II
(74) Attorney, Agent, or Firm — Sughrue Mion, PLLC

(57) ABSTRACT

The invention is directed to accurate calculation of a birefringence of a polymer stretched and oriented. Disclosed is a method for calculating a birefringence of a polymer in an information processing apparatus, having an amorphous state generating step including accepting input of a parameter, generating a model of the polymer on the basis of the parameter, and bringing the model into an amorphous state; a stretching step including stretching the model brought into the amorphous state; a birefringence calculating step including calculating a birefringence of the stretched model; and an outputting step including outputting the birefringence thus calculated.

5 Claims, 7 Drawing Sheets

OTHER PUBLICATIONS

Y. Miyazaki et al., "Prediction of optical properties for stretched polymers using a molecular dynamics method," 53rd Rheology Symposium, Nov. 28-30, 2005.

Y. Kawazoe et al, "Material Science by Computer Simulation", Kyoritsu Shuppan Co., Ltd., 1$^{st}$ edition, Dec. 1, 1996, pp. 55-82.

"Technique for Expecting Physical Characteristics of Liquid Crystal Materials and Development of Ultra-High Birefringence Liquid Crystals", Atsutaka Manabe, Jan. 1, 2002, p. 44-p .49, Partial English translation.

* cited by examiner

Fig.4

| POLYMER | STRETCHING RATIO | STRETCHING TEMPERATURE (°C) | BIREFRINGENCE |
|---|---|---|---|
| POLYSTYRENE | 3 | 105 | $-1.6 \times 10^{-2}$ |
| ETHYLENE/ NORBORNENE COPOLYMER | 3 | 150 | $6.4 \times 10^{-3}$ |
| ETHYLENE/ TETRACYCLODODECENE COPOLYMER | 3 | 151 | $8.3 \times 10^{-4}$ |

*Fig.5*

| TYPE OF BOND | BOND POLARIZATION PARAMETER | |
|---|---|---|
| | $b_1$ | $b_2$ |
| C(ALIPHATIC)—C(ALIPHATIC) | 18.8 | 0.2 |
| C(ALIPHATIC)—C(AROMATIC) | 18.8 | 0.2 |
| C(AROMATIC)—C(AROMATIC) | 22.5 | 4.8 |
| C—H | 7.9 | 5.8 |

Fig.6

| POLYMER | STRETCHING RATIO | RESULT OF CALCULATION OF BIREFRINGENCE (WITH ONLY STRETCHING) | ACTUALLY MEASURED VALUE OF BIREFRINGENCE |
|---|---|---|---|
| | | STRETCHING RATE (m/s) | STRETCHING RATE (m/s) |
| | | $5.00 \times 10^2$ | $5.00$ |
| POLYSTYRENE | 3 | $-4.8 \times 10^{-2}$ | $-4.2 \times 10^{-2}$ | $1.67 \times 10^{-3}$ |
| ETHYLENE/NORBORNENE COPOLYMER | 3 | $5.5 \times 10^{-2}$ | $2.7 \times 10^{-2}$ | $-1.6 \times 10^{-3}$ |
| ETHYLENE/TETRACYCLODODECENE COPOLYMER | 3 | $5.3 \times 10^{-2}$ | $1.6 \times 10^{-2}$ | $6.4 \times 10^{-3}$ |
| | | | | $8.3 \times 10^{-4}$ |

Fig.7

| POLYMER | STRETCHING RATIO | RESULT OF CALCULATION OF BIREFRINGENCE STRETCHING RATE $5.00 \times 10^2$ (m/s) | | ACTUALLY MEASURED VALUE OF BIREFRINGENCE STRETCHING RATE $1.67 \times 10^{-3}$ (m/s) |
|---|---|---|---|---|
| | | WITH ONLY STRETCHING | WITH STRETCHING + RELAXATION | |
| POLYSTYRENE | 3 | $-4.8 \times 10^{-2}$ | $-3.1 \times 10^{-2}$ | $-1.6 \times 10^{-3}$ |
| ETHYLENE/ NORBORNENE COPOLYMER | 3 | $5.5 \times 10^{-2}$ | $1.7 \times 10^{-2}$ | $6.4 \times 10^{-3}$ |
| ETHYLENE/ TETRACYCLODODECENE COPOLYMER | 3 | $5.3 \times 10^{-2}$ | $8.4 \times 10^{-4}$ | $8.3 \times 10^{-4}$ |

BIREFRINGENCE CALCULATING METHOD AND BIREFRINGENCE CALCULATING APPARATUS

BACKGROUND OF THE INVENTION

1. Field of the Invention

The present invention relates to a method and apparatus for calculating a birefringence of a polymer.

2. Related Background of the Invention

Production of a new polymer with specific performance by polymerization involves various problems, e.g., a large number of candidate polymers, high cost, difficult synthesis, and so on. For this reason, it is common practice in the field of computer chemistry to create a model of a polymer for an existing or novel substance and to calculate physical properties of the polymer with a computer. This method is also useful in estimation of a structure for designing of a novel polymer.

Some drawn films of polymers exhibit a performance due to double refraction or birefringence caused by stretching. One example of such a performance acquired in this manner is antireflection. Some attempts to calculate a birefringence value have been reported (e.g., Yasushi Aikawa, "Calculation Method to Estimate the Birefringence of Polymers and Their Experimental Validation", Japanese Journal of Polymer Science and Technology (Kobunshi Ronbunshu), Vol. 51, No. 4, pp. 237-243, 1994 (Non-patent Document 1)).

SUMMARY OF THE INVENTION

The method described in the foregoing Non-patent Document 1 is one in which the polarizability of a monomer structure is calculated and then the intrinsic birefringence is calculated, but it fails to take orientation of a polymer into consideration. It, therefore, was infeasible to implement (accurate) calculation of the birefringence of a film stretched and oriented.

The present invention has been accomplished in order to solve the above problem and an object of the invention is to provide a method and apparatus capable of accurately calculating a birefringence of a polymer stretched and oriented.

A birefringence calculating method according to the present invention is a method for calculating a birefringence of a polymer in an information processing apparatus, including: an amorphous state generating step including accepting input of a parameter, generating a model of the polymer on the basis of the parameter, and bringing the model into an amorphous state; a stretching step including stretching the model brought into the amorphous state in the amorphous state generating step; a birefringence calculating step including calculating a birefringence of the model stretched in the stretching step; and an outputting step including outputting the birefringence calculated in the birefringence calculating step.

In the method according to the present invention, the model of the polymer is stretched to be oriented, and then the birefringence of the model is calculated. Therefore, an effect due to the orientation of the polymer is considered, so that it is feasible to accurately calculate the birefringence of the polymer stretched and oriented.

The stretching in the stretching step is preferably an operation of stretching the model in a preset direction, while keeping a volume of the model constant. Since this configuration allows skilled persons to obtain a state fitting an actual polymer, it becomes feasible to calculate the birefringence more accurately.

The stretching step preferably includes relaxing the model stretched. Since this configuration allows skilled persons to obtain a state fitting an actual polymer, it becomes feasible to calculate the birefringence more accurately. The term "relaxing" herein refers to approximating the model to an equilibrium state by calculation.

The relaxing in the stretching step is carried out while the volume of the model is kept constant. Since this configuration allows skilled persons to obtain a state fitting an actual polymer, it becomes feasible to calculate the birefringence more accurately.

The birefringence calculating step preferably includes calculating vectors of interatomic bonds of the model, calculating polarizabilities of the model by use of bond polarization parameters determined by the calculated vectors and types of the interatomic bonds, calculating refractive indices of the model on the basis of the calculated polarizabilities, and calculating the birefringence on the basis of the calculated refractive indices. This configuration permits skilled persons to securely calculate the birefringence of the polymer.

The method further includes a determination step including determining whether the birefringence calculated in the birefringence calculating step satisfies a termination condition set in advance; outputting the birefringence in the outputting step if the termination condition is satisfied; and, if the termination condition is not satisfied, changing the parameter, again generating a model of the polymer on the basis of the changed parameter, and calculating the birefringence. Since this configuration permits skilled persons to know the parameter of a polymer with a desired birefringence, it becomes easier to design polymers.

A birefringence calculating apparatus according to the present invention is an apparatus for calculating the birefringence of a polymer, including: an amorphous state generating part for accepting input of a parameter, generating a model of the polymer on the basis of the parameter, and bringing the model into an amorphous state; a stretching part for stretching the model brought into the amorphous state by the amorphous state generating part; a birefringence calculating part for calculating a birefringence of the model stretched by the stretching part; and an outputting part for outputting the birefringence calculated by the birefringence calculating part.

The present invention involves stretching a model of a polymer to orient it, and calculating the birefringence of the model. The invention, therefore, takes the effect of the orientation of a polymer into consideration, so that it is feasible to accurately calculate the birefringence of a polymer stretched and oriented.

BRIEF DESCRIPTION OF THE DRAWINGS

FIG. 4 is a table of birefringences obtained by experimental measurement.

FIG. 5 is a table of values of bond polarization parameters used in examples of the present invention.

FIG. 6 is a table of birefringences calculated in examples of the present invention.

FIG. 7 is a table of birefringences calculated in examples of the present invention.

DESCRIPTION OF THE PREFERRED EMBODIMENTS

Preferred embodiments of the birefringence calculating method and birefringence calculating apparatus according to the present invention will be described below in detail with reference to the drawings. The same elements will be denoted by the same reference symbols in the description of the drawings, without redundant description.

The birefringence calculating method according to the embodiment described herein calculates a birefringence of a polymer. The calculation of the birefringence is based on molecular dynamics simulation. The polymer as an object for the birefringence calculation may be one, for use in films, sheets, molded products, and so on. The polymer as an object for the birefringence also encompasses a combination of two or more polymers.

Figure 1:
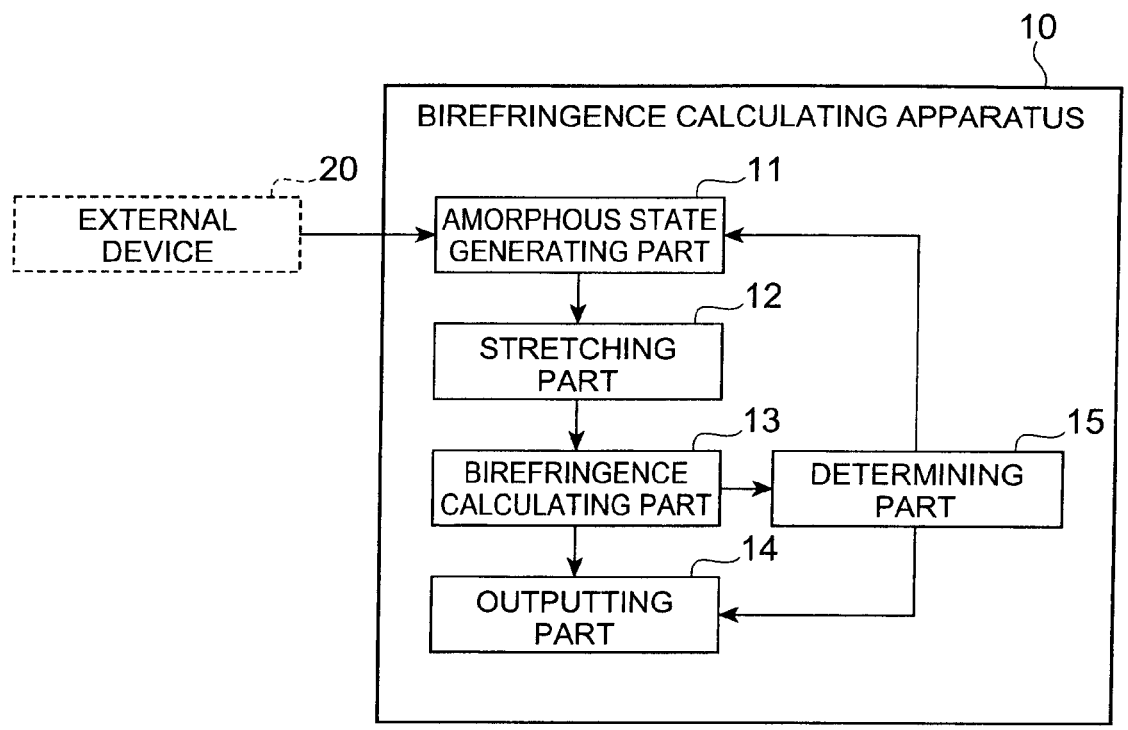
FIG. 1 is a configuration diagram of a birefringence calculating apparatus according to one embodiment of the present invention.

FIG. 1 shows a birefringence calculating apparatus 10 which executes the birefringence calculating method according to the present embodiment. One specific example of birefringence calculating apparatus 10 is an information processing unit such as a workstation or a PC (personal computer). Birefringence calculating apparatus 10 is constituted, for example, of hardware such as a CPU (central processing unit), and memories, and these components operate to exhibit the functions of birefringence calculating apparatus 10 described later. The present method may also be carried out in an alternative manner such that birefringence calculating apparatus 10 executes a program for making the information processing unit execute the birefringence calculating method according to the present embodiment.

As shown in FIG. 1, birefringence calculating apparatus 10 is composed of an amorphous state generating part 11, a stretching part 12, a birefringence calculating part 13, an outputting part 14, and a determining part 15. Birefringence calculating apparatus 10 is connected to an external device 20 and is arranged to accept input of information from external device 20.

Amorphous state generating part 11 accepts input of a parameter, generates a model of a polymer on the basis of the parameter, and brings the model into an amorphous state. The input of the parameter is performed by a user through external device 20. Alternatively, it is also possible to store a parameter from external device 20 in advance, in birefringence calculating apparatus 10 and then use the stored parameter as input.

Stretching part 12 stretches the model brought into the amorphous state by the amorphous state generating part 11. Birefringence calculating part 13 calculates the birefringence of the model stretched by the stretching part 12. Outputting part 14 outputs the birefringence calculated by the birefringence calculating part 13.

Determining part 15 determines whether the sequential processing for the calculation of the birefringence is to be repeated. Specifically, determining part 15 determines whether the birefringence calculated by birefringence calculating part 13 satisfies a termination condition set in advance, and then it makes outputting part 14 output the birefringence if it determined that the termination condition is satisfied, whereas if it is determined that the termination condition is not satisfied, it changes the parameter to generate a model of the polymer again on the basis of the changed parameter, and then causes birefringence calculating part 13 to calculate a birefringence.

The aforementioned processes in the respective components are all carried out as information processing. The specific contents of the respective processes will be described in more detail later.

Figure 2:
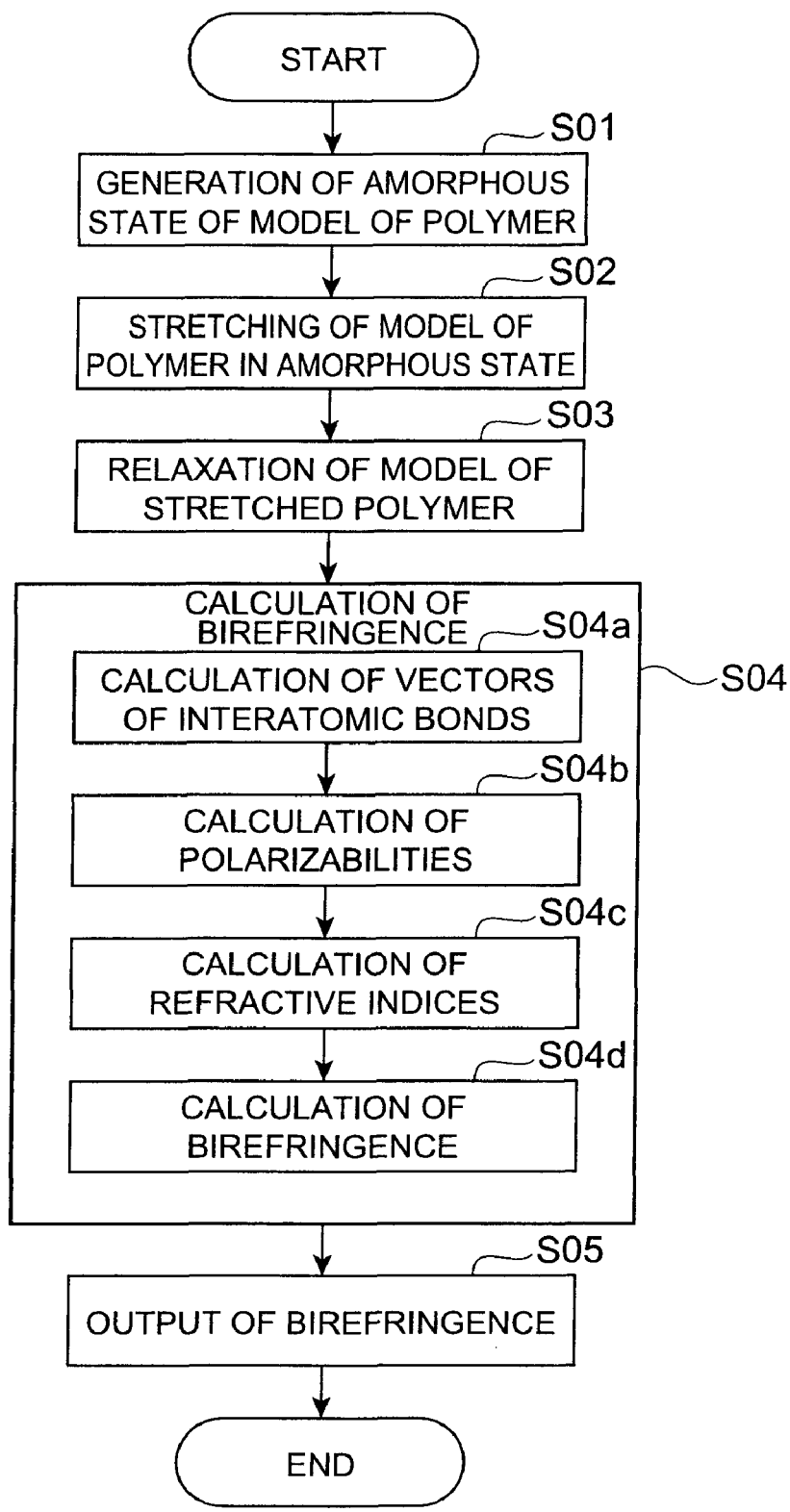
FIG. 2 is a flowchart showing a birefringence calculating method according to one embodiment of the present invention.

The birefringence calculating method according to the present embodiment (the processing executed in birefringence calculating apparatus 10) will be described below with reference to the flowcharts of FIGS. 2 and 3. First, the basic processing of the birefringence calculating method will be described as a first processing with reference to FIG. 2, and then a more practical processing will be described as a second processing with reference to FIG. 3.

[First Processing]

First, amorphous state generating part 11 generates cells as regions where the calculation is carried out, generates a model of a polymer as an object for the birefringence calculation, and brings the model into an amorphous state (S01, amorphous state generating step). The model is generated as follows: amorphous state generating part 11 accepts input of a parameter entered by a user or stored in advance in birefringence calculating apparatus 10, and generates a model on the basis of the parameter. Specific examples of the parameter to be entered include the type of a molecule, the number of monomers, and the number of polymers. Amorphous state generating part 11 is provided in advance with calculation formulae, etc. to express interactions between atoms and between molecules used in the molecular dynamics simulation. The model of the polymer is generated, so that data of the model such as coordinates and potentials of atoms constituting the polymer agree with predetermined conditions.

The model of the polymer may also be generated, for example, in the following manner: a monomer structure is generated using a commercially available molecule structure model, and the model of the polymer is generated on the basis of the monomer structure. In order to attain a model structure calculation without deviation, a preferred shape of the cells is a cube. There are no particular restrictions on the number of monomers constituting the model of the polymer, but a model composed of too few monomers is not preferable because the influence of terminal monomers becomes so great that a large deviation from actual values will occur. From the viewpoint of accuracy, the number of monomers be as large as possible. A model including too many monomers will need a too long calculation time. In view of the above, the number of monomers is preferably from about 30 to about 600. Concerning the boundary of the cells, it is preferable in terms of accuracy of calculation to use a three-dimensional periodic boundary condition such that identical cells are present iteratively in the three-dimensional directions.

The number of polymers is not particularly restricted, either. It, however, is not preferable that a model include too few polymers because influence between polymers is so weak that a large deviation from actual values will occur. The number of polymers is preferably as large as possible in terms of accuracy, but a model including too many polymers will need a too long calculation time. In view of the above, the number of polymers is preferably from about 3 to about 10.

The generation of the amorphous state is carried out by a method using molecular dynamics simulation based on an ensemble. The ensemble designates a calculation technique and is set in advance by a user or the like. Specifically, the ensemble set includes necessary conditions such as temperature, pressure and density, as well as a time step of the simulation, a calculation duration, and so on. It is noted that the molecular dynamics simulation for models is carried out similarly based on the preset ensemble and the above conditions.

In order to generate a uniform amorphous state, the generation of the amorphous state may be performed by a method described, for example, in Kenji Morigami et al., Japanese Journal of Polymer Science and Technology (Kobunshi Ronbunshu), Vol. 53, No. 12, pp. 852-859 (December, 1996). This method consists of (i) a step of performing structure stabilization calculation for a model of a polymer in a low density, using NVE as an ensemble; (ii) a step of thereafter compressing the model at a high pressure, using NPT as an ensemble, and (iii) a step of returning the pressure to ordinary pressure, using NPT as an ensemble. Step (i) is preferably carried out by selecting a volume which provides a density of from 0.01 to 0.1, which is lower than actual. This is because such a condition makes monomers unlikely to contact with each other in preparation of initial structure and facilitates the structure stabilization calculation. In step (ii), the pressure for compressing the polymer model is preferably from 10 MPa to 10000 MPa. The temperature may be set arbitrarily. In step (iii), the pressure may be ordinary pressure and the temperature may be set arbitrarily. In the generation of the amorphous state, in order to attain a model structure calculation without deviation the shape of the cells is preferably a cube. The generation of the amorphous state may also be performed, for example, on the basis of the method described in M. Fukuda and S. Kuwajima, "Molecular Dynamics Simulation of Moisture Diffusion in Polyethylene Beyond 10 ns Duration," J. Chem. Phys., 107, 2149-2159(1997).

Although it is preferable that the time step be as short as possible in order to enhance the accuracy, the shorter the time step, the longer the time necessary for the calculation. Therefore, the time step is preferably from about 0.1 to about 10 fs. The calculation duration is preferably a time before the model becomes steady. The time step and the calculation duration are also similarly set in the processing described below.

The calculation formulae for calculation of interaction forces between atoms and between molecules, and other parameters, which are used in the molecular dynamics simulation, may be those generally known (e.g., those described in Yoshiyuki Kawazoe, Masuhiro Mikami, and Kaoru Ohno, "Material Science by Computer Simulation" Kyoritsu Shuppan Co., Ltd., pp. 55-82). The molecular dynamics simulation of polymer may be performed using bonding potentials and nonbonding potentials. The bonding potentials may include a bond length potential between molecules for keeping a bond length at an equilibrium value, a bond angle potential for keeping a bond angle at an equilibrium angle, and a torsion potential for controlling a dihedral angle that can be taken. The nonbonding potentials may be calculated using the Lennard-Jones potential in a molecule.

Subsequently, stretching part 12 stretches the model brought into the amorphous state in the amorphous state generating step (S02, stretching step). The method for the stretching may be, for example, one selected from a method of giving a deformation tensor to cells, a method of giving a simple extension deformation to cells, a method of effecting, at the time of deformation of cells, an affine transformation corresponding to the cells on coordinates of all the atoms. The method of giving a simple extension deformation to cells is preferably applied because its conditions are close to those of an actual deformation. Specifically, this method is carried out as follows. The stretching is performed according to a method of molecular dynamics simulation based on an ensemble for stretching defined in advance. The ensemble for the stretching is preferably one including a stretch of cells in a preset direction with the volume being kept constant, in consideration of stretching of actual films and sheets. Where a cubic cell is stretched in one direction with its volume being kept constant, the angles of the vertices of the cell is preferably fixed at 90° so that the cell becomes a rectangular parallelepiped. As for the lengths of the sides of the cell in the two directions other than the stretching direction, the lengths are preferably kept equal, in terms of stretching without deviation. The ensemble for stretching with a constant volume is preferably an NVT ensemble. The term "with a constant volume" herein means that the volume of a polymer is set in advance and that the volume is kept constant during the processing of the molecular dynamics simulation in this stretching.

For stretching the model of the polymer, it is necessary to set in advance a stretching rate and a stretching ratio as parameters. In use of an NVT ensemble, the temperature is set in advance as an additional calculation condition. There are no particular restrictions on the temperature, and it may be set arbitrarily. There are no particular restrictions on the volume, but it may be a volume calculated from a density at the temperature set in advance. If the stretching ratio is too large, the polymer will be excessively stretched over the limit. It, therefore, is preferably a moderate value, e.g., not more than 10. The stretching rate may be set arbitrarily and it is possible to adjust the calculation duration through adjustment of the stretching rate. From the viewpoint of calculation accuracy, preferred is a stretching rate closer to a practical stretching rate.

Subsequently, the stretching part 12 relaxes the model stretched (S03, relaxation in the stretching step). The relaxation is performed by a method of molecular dynamics simulation based on the ensemble for relaxation defined in advance. The ensemble for the relaxation is preferably one for relaxing the model with a constant volume, in consideration of stretching of actual films and sheets. When the relaxation is performed with a constant volume, the shape of the cells is preferably kept unchanged. It is preferable to use an NVT ensemble or an NVE ensemble as an ensemble for relaxation with a constant volume.

In use of the NVT ensemble, the volume and temperature are set in advance as conditions for relaxation. There are no particular restrictions on the temperature, and it may be the temperature used during the preceding stretching. There are no particular restrictions on the volume, and it is preferably the volume after the stretching. In use of the NVE ensemble, the volume and energy are set in advance as conditions for relaxation. There are no particular restrictions on the volume and energy, and they are preferably the volume and energy in the stretching. The above stretching step (S02, S03) brings the polymer in the model into an oriented state.

It is noted that the relaxation of the model (S03) is not essential in the present embodiment, and it does not always have to be performed, for example, in the case where a sufficiently accurate birefringence is obtained without execution of the relaxation.

Subsequently, the birefringence calculating part 13 calculates the birefringence of the model stretched and relaxed in the stretching step (S04, birefringence calculating step). The calculation of the birefringence is specifically carried out as described below.

First, vectors of interatomic bonds in the model of the polymer are calculated (S04a). Specifically, the vectors of all the interatomic bonds are calculated from the coordinates of the atoms in the model. Subsequently, polarizabilities in the model of the polymer are calculated using bond polarization parameters determined by the vectors calculated as described above and the types of the interatomic bonds (S04b). Specifically, the polarizabilities $P_x$, $P_y$ and $P_z$ in the directions of the coordinate axes in the model, namely the x-axis direction, the y-axis direction, and the z-axis direction are calculated using the following equations.

$$P_x = \sum (b_1(\cos\theta_x)^2 + b_2(\sin\theta_x)^2)$$
$$P_y = \sum (b_1(\cos\theta_y)^2 + b_2(\sin\theta_y)^2)$$
$$P_z = \sum (b_1(\cos\theta_z)^2 + b_2(\sin\theta_z)^2)$$

(1)

In Eqs (1), $b_1$ and $b_2$ are given values, which are bond polarization parameters determined by the vectors and types of interatomic bonds. Furthermore, $\theta_x$, $\theta_y$, and $\theta_z$ are angles of a bond axis of each interatomic bond relative to the respective coordinate axes x-axis, y-axis, and z-axis). $\Sigma$ represents the sum of the values of the respective interatomic bonds.

Subsequently, refractive indices of the model are calculated on the basis of the polarizabilities $P_x$, $P_y$ and $P_z$ thus calculated (S04c). Specifically, the refractive indices are calculated using the following equations for the respective directions of the coordinate axes.

$$n_x = \sqrt{\frac{8\pi P_x + 3V}{3V - 4\pi P_x}}$$
$$n_y = \sqrt{\frac{8\pi P_y + 3V}{3V - 4\pi P_y}}$$
$$n_z = \sqrt{\frac{8\pi P_z + 3V}{3V - 4\pi P_z}}$$

(2)

In Eqs (2), $n_x$, $n_y$, and $n_z$ represent the refractive indices in the respective directions of the coordinate axes. V represents the molecular volume of one monomer, which is a preset or calculated value.

Subsequently, the birefringence $\Delta n$ is calculated on the basis of the refractive indices $n_x$, $n_y$, and $n_z$ thus calculated (S04d). Specifically, the birefringence $\Delta n$ is calculated using the following equation for each coordinate-axis direction.

$$\Delta n = n_z - \frac{(n_x + n_y)}{2}$$

(3)

In Eq (3), the z-axis direction is the direction of the stretching in S02, and the birefringence $\Delta n$ is the birefringence for the z-axis direction.

Subsequently, the outputting part 14 outputs the birefringence calculated in the birefringence calculating step (S05, outputting step). The output is performed so as to allow the user to reference the information of the birefringence, e.g., by displaying it on a monitor such as a display device equipped in the birefringence calculating apparatus 10. Another output means is to output the information to another device. The birefringence may be outputted together with information about the structure of the polymer as an object for the calculation of the birefringence.

As described above, the birefringence calculating method of the present embodiment involves stretching and orienting a model of a polymer and calculating the birefringence of the model. Therefore, the influence of orientation of the polymer is taken into consideration, and it is thus feasible to accurately calculate the birefringence of the polymer stretched and oriented.

The birefringence calculated in this manner is used for designing of a new polymer to be used in films, sheets, and the like. According to the present embodiment, since a birefringence can be obtained through calculation by an information processor unit, it is possible to obtain the birefringence more quickly and more cheaply than by actually synthesizing a polymer and measuring its birefringence. Therefore, the present embodiment facilitates synthesis of a polymer with a desired birefringence.

When stretching a model in one preset direction with a constant volume as in the present embodiment, it is possible to obtain a state fitting an actual polymer, leading to a more accurate calculations of birefringence. Further, when relaxing the stretched model with a constant volume, it is possible to obtain a state fitting an actual polymer, resulting in a more accurate calculation of birefringence. If the relaxation is preformed while the volume of the model is kept constant, it is possible to obtain a state fitting an actual polymer, enabling a much more accurate calculation of a birefringence.

When a birefringence is obtained by calculating a refractive indices and then calculating a birefringence on the basis of the refractive indices as in the present embodiment, the birefringence of the polymer can be calculated securely.

[Second Processing]

The second processing is a processing procedure for searching for a polymer with a desired birefringence using above-described the first processing, which is a processing for calculating a birefringence of a polymer.

Figure 3:
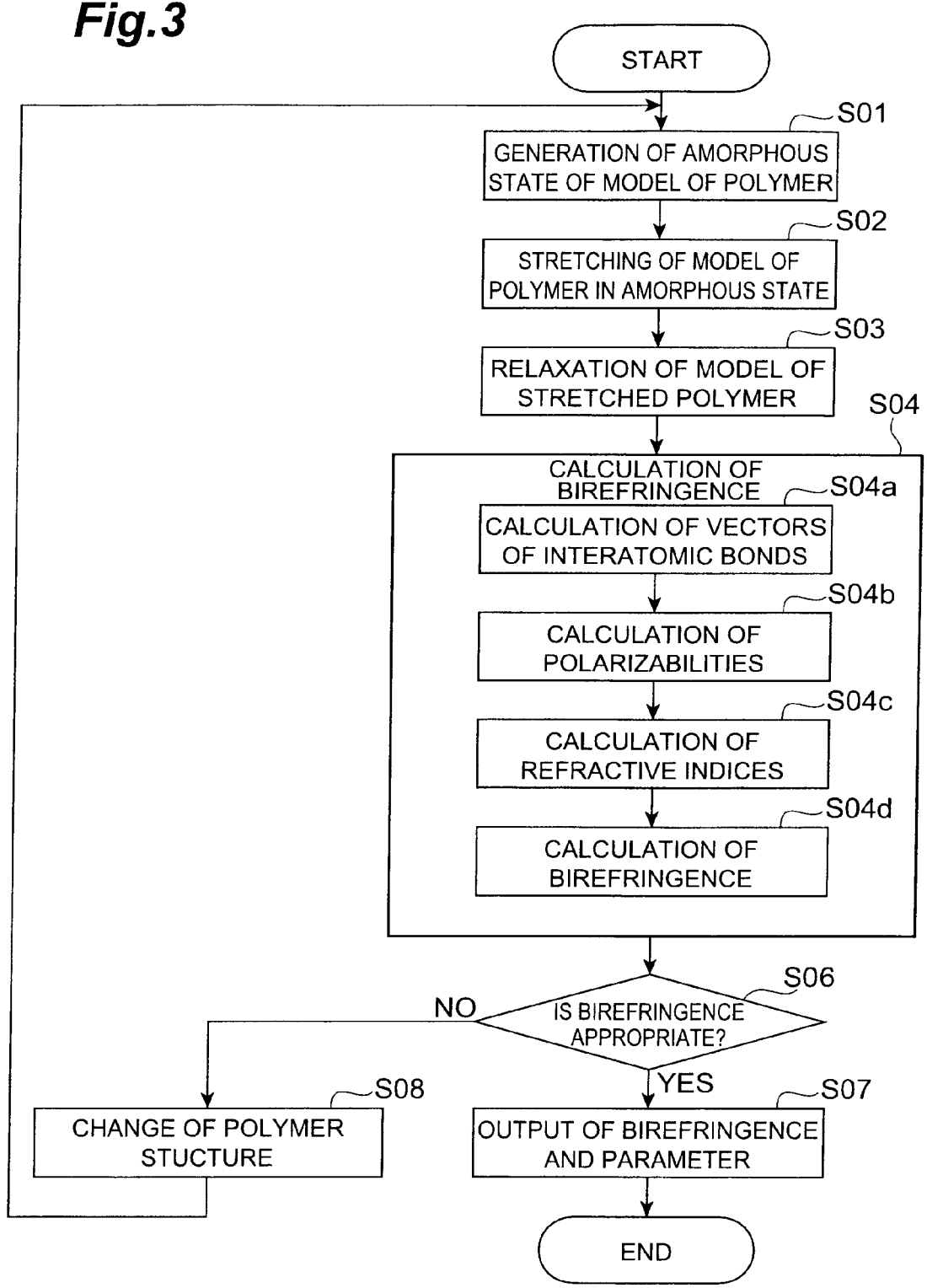
FIG. 3 is a flowchart showing a birefringence calculating method according to another embodiment of the present invention.

As shown in FIG. 3, the processes from the generation of the amorphous state of a model of a polymer (S01) to the calculation of a birefringence (S04) are similar to those in the first processing. In the second processing, in order to change a parameter and again generate a model of the polymer, a plurality of parameters are entered in advance into the birefringence calculating apparatus 10 and stored (on a memory) in the birefringence calculating apparatus 10.

One example of the parameter which is to be changed is a parameter about a monomer for forming a polymer. The monomer stated herein is not a monomer molecule, but means a monomeric unit. Specific examples of the parameter about the monomer include the types of atoms constituting the monomer, the coordinates of respective atoms, and the types of bonds between atoms. Specific examples of the monomer used in the calculation of a birefringence include α-olefin units such as an ethylene unit, a propylene unit, and a 1-butene unit, units having an alicyclic hydrocarbon group, such as a norbornene unit and dimethano-octahydronaphthalene unit, units having an aromatic hydrocarbon group, such as a styrene unit and a 2-vinyl naphthalene unit, and units having an ether group, such as a methylene oxide unit, an ethylene oxide unit, and a propylene oxide unit. The monomer initially used in the calculation of a birefringence may be arbitrarily selected.

After completion of the above steps (S01-S04), the determining part 15 determines whether the resulting birefringence satisfies a preset termination condition (S06, determining step). Specifically, the preset termination condition is, for example, that the birefringence is in a range defined by an upper threshold and a lower threshold set in advance. These thresholds are memorized in advance in the determining part 15.

When the determining part 15 determines that the termination condition is not satisfied, the determining part 15 controls the amorphous state generating part 11 to change the value of the parameter and generate another polymer model (S08, determining step). Specifically, the structure of the polymer, e.g., the monomer structure in the polymer, is modified. The monomer structure in the polymer may be modified by, for example, changing the monomers forming the polymer to another kind of monomers oref copolymerizing another kind of monomers. The monomers to be used as such another kind of monomers are selected from the monomers the information of which is stored in advance as described above. The structure of the polymer may also be modified, for example, by changing the arrangement of the monomers forming the polymer or by forming branches in the polymer chain.

When the calculated birefringence is larger than the range of desired values (namely when it exceeds the upper threshold), the monomer to be selected is preferably a unit having an aromatic hydrocarbon group. The unit having an aromatic hydrocarbon group is effective in decreasing the birefringence, and the effect becomes more significant with increase in the number of aromatic rings. In the case of copolymerization, the effect becomes more significant with increase in the amount of the monomer to be copolymerized. Examples of the unit having an aromatic hydrocarbon group include a styrene unit, and a 2-vinyl naphthalene unit.

When the calculated birefringence is smaller than the range of desired values (namely when the birefringence is smaller than the lower threshold), the monomer to be selected is preferably a unit having an ether group. The unit having an ether group is effective in increasing the birefringence, and the effect becomes more significant with increase in the number of oxygen atoms originating in the ether group. In the case of copolymerization, the effect becomes more significant with increase in the amount of the monomer to be copolymerized. Examples of the unit having the ether group include a methylene oxide unit, and an ethylene oxide unit.

The information about the monomer selected, and about how to change the monomer structure (e.g. change of monomers or copolymerization of monomers), about how to arrange monomers (e.g. sequential order or steric orientation of monomers), and about the number, position, length or the like of branches is stored in advance in the determining part 15 and the monomer structure is changed on the basis of the information. After a polymer is generated again by the amorphous state generating part 11, the sequential processes (S01-S04) to calculate a birefringence are carried out again.

When the determining part 15 determines that the termination condition is satisfied, the information of the birefringence is transmitted to the outputting part 14 and is outputted from the outputting part 14 (S07, outputting step). On the occasion of outputting, the parameter of the polymer as the object for the birefringence calculation is also outputted in addition to the information of the birefringence. Specifically, the information outputted may be the information of the monomer forming the polymer; where the polymer is a copolymer, the information outputted may be the copolymerization ratios of the monomers forming the polymer, the sequential order of the monomers and the steric orientation of the monomers; and where branches are formed, the information may be the number, position, length or the like of the branches, or the like. Making reference to such information, it is much easier to design a polymer with a desired birefringence.

The following will describe examples of calculation of birefringences of polymers by the birefringence calculating method of the present embodiment. Birefringences of polymers were actually measured and the measured birefringences were compared with the birefringences calculated by the birefringence calculating method of the present embodiment. The actual measurement and calculation of birefringences were conducted for three polymers below.

(1) Polystyrene G440K (available from Japan Polystyrene Inc.). Prior to actual measurement, the material was subjected to the following treatment. It was preheated at 230° C. for five minutes by a press molding machine, and thereafter it was pressed under the pressure of 100 kgf/cm$^2$ for one minute. Thereafter, it was moved to the press molding machine controlled at 30° C., and was left to stand for five minutes. Then a film 160 mm square and 150 μm thick was made from the material.

(2) Ethylene/norbornene copolymer Topas6013 (available from Ticona). Prior to actual measurement, the material was subjected to the following treatment. It was preheated at 280° C. for five minutes by a press molding machine, and thereafter it was pressed under the pressure of 100 kgf/cm$^2$ for one minute. Thereafter, it was moved to the press molding machine controlled at 30° C., and was left to stand for five minutes. Then a film 160 mm square and 150 Urn thick was made from the material.

(3) Ethylene/tetracyclododecene copolymer APEL5014D (available from Mitsui Chemicals, Inc.). Prior to actual measurement, the material was subjected to the following treatment. It was preheated at 280° C. for five minutes by a press molding machine, and thereafter it was pressed under the pressure of 100 kgf/cm$^2$ for one minute. Thereafter, it was moved to the press molding machine controlled at 30° C., and was left to stand for five minutes. Then a film 160 mm square and 150 μm thick was made from the material.

The birefringences of the three polymers described above were actually measured as follows. First, each film obtained by pressing was cut in the size of length 70 mm (stretching direction)×width 30 mm to obtain a test piece. Subsequently, a tensile testing machine AGS500D (with a constant-temperature bath, available from Shimadzu Corporation) was used to control the constant-temperature bath to +10° C. from the stretching temperature. Each film test piece was set with a chuck distance of 30 mm, and was stretched at a stretching rate of $1.67 \times 10^{-3}$ [m/s] to a predetermined stretching ratio. After cooling, the phase difference was measured by an analyzer KOBRA21ADH (available from Oji Scientific Instruments). After the stretching, the thickness was measured and the birefringence was calculated according to birefringence=phase difference/thickness. The results of actual measurements are presented in the table of FIG. 4.

Next described are examples of calculation of the birefringences of the above three polymers by the birefringence calculating method of the present embodiment. The software package for molecular simulation "J-OCTA" (The Japan Research Institute, Limited) was used for generation of models of the polymers. In addition, AMBER was used as the force field parameter in generation of the models. The molecular dynamics simulation in each step was conducted using the COarse-Grained molecular dynamics program by NAgoya Cooperation "COGNAC" (the joint project of industry and academia funded by Ministry of Economy, Trade and Industry, Japan) which is the simulation engine of "OCTA" being the integrated simulator for soft materials. The calculation of the birefringence will be described below for each polymer.

(1) Concerning polystyrene, the shape of the cell was a cube and the initial structure of the model was generated from four polymers made of 50 monomers. The boundary condition was the three-dimensional periodic boundary condition. For this model, the molecular dynamics simulation was conducted under the conditions of an NVE ensemble, the initial temperature of 378 K, the pressure of 0.05 atm, the time step of 2 fs, and the calculation duration of 20 ps, and thereafter the molecular dynamics simulation was conducted under the conditions of an NPT ensemble, the temperature of 378 K, the pressure of 3300 MPa, the time step of 2 fs, and the calculation duration of 20 ps, to bring the model into an amorphous state. The shape of the cell was always kept as a cube.

The model of the amorphous structure was subjected to the molecular dynamics simulation to stretch the cell at a constant rate of $5.00 \times 10^2$ [m/s] in the z-axis direction, under the conditions of an NVT ensemble, a temperature of 378 K, the size of the cell of 3.38 nm on each side, a density of 0.9, a time step of 2 fs, and a calculation duration of 30 ps. In the stretching, the angles of the vertices were fixed at 90° so as to keep the cell in a rectangular parallelepiped. The lengths of the sides of the cell in the x-axis direction and the y-axis direction other than the stretching direction were kept equal. A ratio of the cell length $z_t$ in the z-axis direction at the time t to the initial cell length $z_0$, represented by an equation below, is defined as a stretching ratio $\lambda$.

$$\lambda = z_t/z_0$$

(2) The molecular dynamics simulation to stretch the model in the same method as in (1), except for using a constant speed of 5 [m/s] and a calculation duration of 3000 ps, was carried out using the model of the amorphous structure of polystyrene.

The results of molecular dynamics simulations were saved at intervals of 400 fs, and vectors of interatomic bonds were calculated from the coordinates of the atoms present in the model. The values presented in the table of FIG. 5 (the values described in K. G. Denbigh; Trans, Faraday Soc., 36, 936 (1940)) were used as the bond polarization parameters used in the calculation of polarizabilities. The molecular volume (V in Eq (2)) used was 98, which is a calculated value described in D. W. Van Krevelan; "Properties of Polymers," $2^{nd}$ ed. Elsevier, Amsterdam (1976), pp. 56-59. The birefringences calculated under the above-described conditions are those without the relaxation in the stretching step.

(3) It cases where relaxation is executed in a stretching step, a birefringence is determined as follows. Namely, in the stretching step of (1), the molecular dynamics simulation under the conditions of an NVE ensemble, the initial temperature of 378 K, a time step of 2 fs, and a calculation duration of 1000 ps is carried out from the stretched state to achieve a stretching ratio of 3. The shape of the cell is fixed. An average is calculated from birefringences calculated at intervals of 20 ps during the period from 800 ps to 1000 ps (a period in which the birefringence is almost steady) in the calculation duration, and the average is defined as the birefringence with relaxation.

(4)-(6) The initial structure of the model consisting of four polymers each having 25 ethylene units and 25 norbornene units was generated for the alternating copolymer of ethylene and norbornene (ethylene/norbornene copolymer). The initial temperature in the molecular dynamics simulation was 423 K. The molecular volume (V in Eq (2)) was 121.65, which is a value calculated using the calculation parameters for the molecular volume described in D. W. Van Krevelan; "Properties of Polymers," $2^{nd}$ ed. Elsevier, Amsterdam (1976), pp. 56-59. The birefringence was calculated in the same manner as in the polystyrene case (1) to (3) except that the model of the amorphous structure had a density of 1.02 and the cell had a size of 2.71 nm on each side.

(7)-(9) The Initial structure of the model consisting of four polymers each having 32 ethylene units and 16 tetracyclododecene units was generated for the copolymer of ethylene and tetracyclododecene (ethylene/tetracyclododecene copolymer). The sequence of ethylene and tetracyclododecene was assumed to be repetitions of ethylene/tetracyclododecene/ethylene. The initial temperature in the molecular dynamics simulation was 424 K. The molecular volume was 177.5, which is a value calculated using the calculation parameters for the molecular volume described in D. W. Van Krevelan; "Properties of Polymers," $2^{nd}$ ed. Elsevier, Amsterdam (1976), pp. 56-59. The birefringence was calculated in the same manner as in the polystyrene case (1)-(3) except that the model of the amorphous structure had a density of 1.04 and a cell had the size of 2.94 nm on each side.

The birefringences of the three polymers are presented for each of the case with only stretching in the stretching step and the case with relaxation after stretching in the tables of FIG. 6 and FIG. 7 (along with the actually measured values described above). It is apparent from the values presented in the tables of FIGS. 6 and 7 that the birefringence calculating method of the present embodiment enables accurate calculation of birefringence values. In addition, when executing relaxation after stretching, it is possible to calculate a birefringence value more accurately.

What is claimed is:

1. A method for calculating a birefringence of a polymer in a birefringence calculating apparatus comprising a processor and a memory, comprising:
    an amorphous state generating step comprising accepting input of a parameter from an external device, generating a model of the polymer on the basis of the parameter, and bringing the model into an amorphous state;
    a stretching step comprising stretching the model brought into the amorphous state in the amorphous state generating step, carried out by the birefringence calculating apparatus;
    a birefringence calculating step comprising calculating a birefringence of the model stretched in the stretching step;
    an outputting step comprising outputting the birefringence calculated in the birefringence calculating step to a device, carried out by the birefringence calculating apparatus; and
    a determination step comprising determining whether the birefringence calculated in the birefringence calculating step satisfies a termination condition set in advance;
    outputting the birefringence in the outputting step when the termination condition is satisfied; and, when the termination condition is not satisfied, changing the parameter relating to the polymer, again generating a model of the polymer on the basis of the changed parameter, and calculating a birefringence, wherein simulation comprising the generating, stretching, calculating, outputting and determining steps is repeated, wherein different parameters apply to the generating step until a termination condition is met, and
    wherein the parameter change relating to the polymer is a change of monomers forming the polymer, or copolymerization of another kind of monomer,
    wherein the termination condition is that the birefringence is in a range defined by a preset upper threshold and a preset lower threshold, and
        when the calculated birefringence is larger than the upper threshold, side chain(s) having an aromatic hydrocarbon group is/are subject to a change in parameter relating to the monomer to lower birefringence,
            wherein the change in parameter relating to the monomer includes increasing the content of the aromatic hydrocarbon group and increasing the number of aromatic rings of the side chain(s) of the monomer, and when the calculated birefringence is smaller than the lower threshold, a main chain unit having an ether group is subject to a change in parameter relating to the monomer to increase birefringence, wherein the change in parameter relating to the monomer includes increasing the content of the ether group and increasing the number of oxygen atoms originating in the ether group of the main chain unit.

2. The method according to claim 1, wherein the stretching in the stretching step is stretching of the model in a preset direction, while keeping a volume of the model constant.

3. The method according to claim 1, wherein the stretching step comprises relaxing the model stretched.

4. The method according to claim 3, wherein the relaxing in the stretching step is carried out while a volume of the model is kept constant.

5. The method according to claim 1, wherein the birefringence calculating step comprises calculating vectors of interatomic bonds of the model, calculating polarizabilities of the model by use of bond polarization parameters determined by the calculated vectors and types of the interatomic bonds, calculating refractive indices of the model on the basis of the calculated polarizabilities, and calculating the birefringence on the basis of the calculated refractive indices.

* * * * *